(12) United States Patent
Roca et al.

(10) Patent No.: US 6,414,025 B1
(45) Date of Patent: Jul. 2, 2002

(54) UTILIZATION OF 2-HYDROXY-4-TRIFLUOROMETHYLBENZOIC ACID DERIVATIVES AS INHIBITORS OF THE ACTIVATION OF THE NUCLEAR TRANSCRIPTION FACTORS NF-κβ

(75) Inventors: Manuel Merlos Roca; Alberto Fernandez De Arriba; Fernando Cavalcanti De Maria, all of Barcelona; Agustí Miralles Acosta, Granollers; Mariano Sanchez Crespo, Valladolid; Julián Garcia Rafanell; Javier Forn Dalmau, both of Barcelona, all of (ES)

(73) Assignee: J. Uriach & Cia, S.A., Barcelona (ES)

( * ) Notice: Subject to any disclaimer, the term of this patent is extended or adjusted under 35 U.S.C. 154(b) by 0 days.

(21) Appl. No.: 09/701,270

(22) PCT Filed: May 26, 1999

(86) PCT No.: PCT/ES99/00154

§ 371 (c)(1),
(2), (4) Date: Feb. 20, 2001

(87) PCT Pub. No.: WO99/61030

PCT Pub. Date: Dec. 2, 1999

(30) Foreign Application Priority Data

May 27, 1998 (ES) .............................................. 9801154

(51) Int. Cl.[7] .............................................. A61K 31/60

(52) U.S. Cl. ...................................................... 514/568
(58) Field of Search .......................................... 514/568

(56) References Cited

U.S. PATENT DOCUMENTS 4,096,252 A * 6/1978 Barra et al. .................. 424/230
6,040,341 A * 3/2000 Del Soldato et al. ....... 514/509

OTHER PUBLICATIONS

Garcia–Rafanell, J. Neuropathol. Exp. Neurol., vol. 54, pp. 365–395 (1995).*
De lla Cruz et al, Eur. J. Clin. Pharmacol., vol. 47, #6, pp. 497–502 (1995).*
Webb, Circulation, vol. 91, #7, pp. 1914–1917 (1995).*

* cited by examiner

*Primary Examiner*—James H Reamer
(74) *Attorney, Agent, or Firm*—Rothwell, Figg, Ernst & Manbeck

(57) ABSTRACT

The invention relates to the use of 2-hydroxy-4-trifluoromethylbenzoic acid derivatives as inhibitors of the activation of the nuclear transcription factor NF-κB. The invention also relates to the utilization of 2-hydroxy-4-trifluoromethylbenzoic acid derivatives for the preparation of medicaments to treat or prevent of pathologies associated to the activation of NF-κB and/or the expression of genes which are dependent on or regulated by, at least partially, NFκB in mammals, including humans.

15 Claims, 9 Drawing Sheets

UTILIZATION OF 2-HYDROXY-4-TRIFLUOROMETHYLBENZOIC ACID DERIVATIVES AS INHIBITORS OF THE ACTIVATION OF THE NUCLEAR TRANSCRIPTION FACTORS NF-κβ

FIELD OF THE INVENTION

The present invention relates to inhibitors of the nuclear transcription factor kappaB (NF-κB) and to their use in therapy. Specifically, the present invention relates to the use of 2-hydroxy-4-trifluoromethylbenzoic acid derivatives to inhibit the activation of the transcription factor NF-κB.

DESCRIPTION OF PRIOR ART

The control of the expression of proteins plays a key role both in the maintenance of the normal function of cells and hence of organisms, as well as in the development of pathological processes. This control is effected through the so-called transcription factors. One of these factors is the group of proteins known as nuclear transcription factor NF-κB, formed by a family of intimately related dimeric complexes. NF-κB exists in an inactive form in the cytoplasm of many types of cells. In response to a stimulus, it becomes activated and is then translocated to the nucleus, where it binds to DNA and regulates the transcription of various genes. The activation of NF-κB can be induced by several agents such as inflammatory cytokines (for example, tumor necrosis factor-alfa (TNF-α) and interleukin-1beta (IL-1β)), mitogens, bacterial lipopolysaccharides (LPS), viruses, oxidants (for example, $H_2O_2$ and ozone), phorbol esters and ultraviolet light. Among the various genes whose expression is regulated by NF-κB, many genes involved in immune and inflammatory responses are included. Thus, among others, NF-κB regulates the expression of proinflammatory cytokines such as IL-1β, interleukin-2 (IL-2), interleukin-6 (IL-6), TNF-α and granulocyte-macrophage colony stimulating factor (GM-CSF); chemokines such as interleukin-8 (IL-8), RANTES, macrophage inflammatory protein-1α (MlP-1α), monocyte chemotactic protein-1 (MCP-1) and eotaxin; inflammatory enzymes such as inducible nitric oxide synthase (iNOS), cyclooxygenase-2 (COX-2), 5-lipoxygenase (5-LO) and cytosolic phospholipase $A_2$ (cPLA$_2$); adhesion molecules such as intercellular adhesion molecule-1 (ICAM-1), vascular cell adhesion molecule-1 (VCAM-1) and E-selectin; and receptors such as the interleukin-2 receptor and the T-cell receptor (P. J. Barnes and I. M. Adcock, *Trends Pharmacol. Sci.* 1997, 18, 46–50).

Dysfunctions in the activation of NF-κB and its dependent genes have been associated with several pathologies such as acute inflammation, septic shock, transplant rejection, radiation damage, ischemia and reperfusion damage and neurodegenerative diseases (P. A. Baeuerle and T. Henkel, *Annu. Rev. Immunol.* 1994, 12, 141–179), asthma and other chronic inflammatory diseases (P. J. Barnes and I. M. Adcock, *Trends Pharmacol. Sci.* 1997, 18, 46–50), osteoporosis (Y. Abu-Amer and M. Mehrad Tondravi, *Nature Med.* 1997, 3(11), 1189–1190), and cancer (M. A. Sovak et al., *J. Clin. Invest.* 1997, 100 (12), 2952–2960). Moreover, elevated levels of NF-κB have been detected in synovial tissue of patients with rheumatoid arthritis (H. Asahara et al., *Biochem. Mol Biol. Int.,* 1995, 37(5), 827–32), in central nervous system samples of multiple sclerosis patients (D. Gveric et al., *J. Neuropathol. Exp. Neurol.* 1998, 57(2), 168–78) and in samples of atherosclerotic tissue (K. Brand et al., *J. Clin. Invest.* 1996, 97(7), 1715–22), and it has been described that amyloid β peptide, which accumulates in plaques of Alzheimer patients, activates NF-κB in central nervous system cells (C. Behl et al., *Cell* 1994, 77, 817–827). A high increase in the nuclear translocation of NF-κB has also been observed in dopaminergic neurons of patients with Parkinson's disease (S. Hunot et al., *Proc. Natl. Acad. Sci. USA* 1997, 94(14), 7531–7536). Furthermore, NF-κB has also been reported to be involved in the transcriptional activation of viruses such as human immunodeficiency virus (HIV), cytomegaloviruses, adenoviruses and herpesviruses.

On the other hand, it has been shown that the cytokines, inflammatory enzymes, adhesion molecules and other proteins whose expression is regulated by NF-κB play an important role in a broad range of disorders such as inflammation; asthma; adult respiratory distress syndrome (ARDS); immunoinflammatory and autoimmune diseases such as rheumatoid arthritis, multiple sclerosis, psoriasis, inflammatory bowel disease, lupus and glomerulonephritis; arthrosis; septic shock; atherosclerosis; cancer; osteoporosis; preterm labour; transplant rejection; neurodegenerative diseases such as dementia, including Alzheimer's disease, Parkinson's disease and amyotrophic lateral sclerosis; and viral infections.

In view of the above, the agents which are able to modulate the activity of the transcription factor NF-κB and/or the expression of genes which are dependent on this transcription factor could be of great utility as therapeutic agents for the treatment or prevention of the above-mentioned disorders. It is thus of great interest to find agents which are capable of regulating NF-κB activity.

2-Acetyloxy-4-trifluoromethylbenzoic acid, better known by its International Nonproprietary Name (INN) triflusal, is a platelet aggregation inhibitor marketed for the treatment of thromboembolic diseases under the trademark Disgren®. Its main metabolite, 2-hydroxy-4-trifluoromethylbenzoic acid (also known by the acronym HTB), also possesses a remarkable activity as platelet antiaggregant. Both compounds are described in U.S. Pat. No. 4,096,252.

The present inventors have found that, surprisingly, both triflusal and its metabolite, HTB, inhibit NF-κB activation. Moreover, it has been found that both compounds are potent inhibitors of the expression of genes that are transcriptionally regulated by NF-κB. Due to this new activity now discovered, triflusal and HTB are potentially useful in the treatment or prevention of disorders where the activation of NF-κB and its dependent genes is involved, such as those mentioned above.

DESCRIPTION OF THE INVENTION

The present invention is based upon the finding that triflusal and its metabolite, HTB, are potent inhibitors of the activation of the transcription factor NF-κB. As mentioned above, NF-κB is an ubiquitous transcription factor that acts by binding to DNA, activating in this manner the expression of various genes, many of them involved in the immune and inflammatory response. The present invention shows that triflusal and HTB inhibit the activation of NF-κB induced by various agents such as TNF-α, immune complexes and LPS in several types of cells, such as human umbilical vein endothelial cells (HUVEC), macrophages and monocytes. Moreover, it is also shown that triflusal and HTB inhibit the expression of several proteins in whose transcriptional regulation NF-κB is involved, such as for example VCAM-1, iNOS, COX-2, MCP-1 and TNF-α. Therefore, triflusal and HTB are useful as therapeutic or preventive agents in those pathological situations where NF-κB and/or the proteins whose expression is regulated by this transcription factor are involved.

Triflusal and HTB can be generically represented by means of formula I:

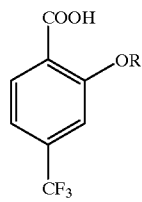

(I)

wherein R represents hydrogen (HTB) or COCH₃ (triflusal).

It is an object of the present invention to provide the use of a compound of formula I for the manufacture of a medicament useful for inhibiting the activation of the transcription factor NF-κB. The use of a pharmaceutically acceptable salt of a compound of formula I or of a prodrug thereof are also encompassed within the scope of the present invention.

Another object of the present invention is to provide the use of a compound of formula I or a pharmaceutically acceptable salt or a prodrug thereof for the manufacture of a medicament useful for inhibiting the expression of genes which are dependent on and/or regulated by, at least partially, the transcription factor NF-κB. In a preferred embodiment, the gene encodes IL-1β, IL-2, IL-6, TNF-α, GM-CSF, IL-8, RANTES, MIP-1α, MCP-1, eotaxin, iNOS, COX-2, 5-LO, cPLA₂, ICAM-1, VCAM-1, E-selectin, IL-2 receptor or T-cell receptor, and more preferably encodes VCAM-1, iNOS, COX-2, MCP-1 or TNF-α.

It is also an object of the present invention to provide the use of a compound of formula I or a pharmaceutically acceptable salt or a prodrug thereof for the manufacture of a medicament for the treatment or prevention of disorders associated with the activation of the transcription factor NF-κB and/or the expression of genes which are dependent on this transcription factor. In a preferred embodiment, the disorder is inflammation; asthma; adult respiratory distress syndrome (ARDS); immunoinflammatory and autoimmune diseases such as rheumatoid arthritis and other arthritic conditions, multiple sclerosis, psoriasis, inflammatory bowel disease, lupus and glomerulonephritis; arthrosis; septic shock; atherosclerosis; cancer; osteoporosis; preterm labour; transplant rejection; neurodegenerative diseases such as dementia, including Alzheimer's disease, Parkinson's disease and amyotrophic lateral sclerosis; and viral infections.

It is also an object of the present invention to provide the use of a compound of formula I or a pharmaceutically acceptable salt or a prodrug thereof for the manufacture of a medicament useful for inhibiting the expression of COX-2.

Another object of the present invention is to provide the use of a compound of formula I or a pharmaceutically acceptable salt or a prodrug thereof for the manufacture of a medicament for the treatment or prevention of diseases mediated by COX-2. In a preferred embodiment, the disease mediated by COX-2 is rheumatoid arthritis and other arthritic conditions, arthrosis, preterm labour, dementia or cancer.

It is also an object of the present invention to provide the use of a compound of formula I or a pharmaceutically acceptable salt or a prodrug thereof for the manufacture of a medicament useful for inhibiting the expression of VCAM-1.

It is also an object of the present invention to provide the use of a compound of formula I or a pharmaceutically acceptable salt or a prodrug thereof for the manufacture of a medicament for the treatment or prevention of diseases mediated by VCAM-1. In a preferred embodiment, the disease mediated by VCAM-1 is atherosclerosis, rheumatoid arthritis, lupus, multiple sclerosis, inflammatory bowel disease, asthma, allergic rhinitis and tumor metastasis.

Another object of the present invention is to provide the use of a compound of formula I or a pharmaceutically acceptable salt or a prodrug thereof for the manufacture of a medicament useful for inhibiting the expression of iNOS.

It is also an object of the present invention to provide the use of a compound of formula I or a pharmaceutically acceptable salt or a prodrug thereof for the manufacture of a medicament for the treatment or prevention of diseases mediated by iNOS. In a preferred embodiment, the disease mediated by iNOS is inflammation, septic shock, inflammatory bowel disease and neurodegenerative diseases.

It is also an object of the present invention to provide the use of a compound of formula I or a pharmaceutically acceptable salt or a prodrug thereof for the manufacture of a medicament useful for inhibiting the expression of TNF-α.

Another object of the present invention is to provide the use of a compound of formula I or a pharmaceutically acceptable salt or a prodrug thereof for the manufacture of a medicament for the treatment or prevention of diseases mediated by TNF-α. In a preferred embodiment, the disease mediated by TNF-α is rheumatoid arthritis, rheumatoid spondylitis, gouty arthritis and other arthritic conditions, arthrosis, sepsis, septic shock, endotoxic shock, toxic shock syndrome, adult respiratory distress syndrome, cerebral malaria, chronic pulmonary inflammatory disease, silicosis, pulmonary sarcoidosis, pulmonary fibrosis, hepatitis, osteoporosis and other bone resorption diseases, reperfusion injury, transplant rejection, multiple sclerosis, lupus, fever and myalgias due to infections, cachexia, acquired immune deficiency syndrome (AIDS), inflammatory bowel disease and pyresis.

It is also an object of the present invention to provide the use of a compound of formula I or a pharmaceutically acceptable salt or a prodrug thereof for the manufacture of a medicament useful for inhibiting the expression of MCP-1.

It is also an object of the present invention to provide the use of a compound of formula I or a pharmaceutically acceptable salt or a prodrug thereof for the manufacture of a medicament for the treatment or prevention of diseases mediated by MCP-1. In a preferred embodiment, the disease mediated by MCP-1 is atherosclerosis, glomerulonephritis, rheumatoid arthritis, pulmonary fibrosis, restenosis, asthma, psoriasis, inflammatory bowel disease, multiple sclerosis and transplant rejection.

It is also an object of the present invention to provide the use of a compound of formula I or a pharmaceutically acceptable salt or a prodrug thereof for the manufacture of a medicament for the treatment or prevention of neurodegenerative diseases, particularly dementia, Parkinson's disease and amyotrophic lateral sclerosis.

It is also an object of the present invention to provide the use of a compound of formula I or a pharmaceutically acceptable salt or a prodrug thereof for the manufacture of a medicament for the treatment or prevention of immunoinflammatory and autoimmune diseases, preferably rheumatoid arthritis and other arthritic conditions, multiple sclerosis, psoriasis, inflammatory bowel disease, lupus and glomerulonephritis.

It is also an object of the present invention to provide the use of a compound of formula I or a pharmaceutically acceptable salt or a prodrug thereof for the manufacture of a medicament for the treatment or prevention of arthrosis.

It is also an object of the present invention to provide the use of a compound of formula I or a pharmaceutically acceptable salt or a prodrug thereof for the manufacture of a medicament for the treatment or prevention of cancer.

It is also an object of the present invention to provide the use of a compound of formula I or a pharmaceutically acceptable salt or a prodrug thereof for the manufacture of a medicament for the treatment or prevention of atherosclerosis.

It is also an object of the present invention to provide the use of a compound of formula I or a pharmaceutically acceptable salt or a prodrug thereof for the manufacture of a medicament for the prevention of preterm labour.

It is also an object of the present invention to provide the use of a compound of formula I or a pharmaceutically acceptable salt or a prodrug thereof for the manufacture of a medicament for the treatment or prevention of inflammation.

It is also an object of the present invention to provide the use of a compound of formula I or a pharmaceutically acceptable salt or a prodrug thereof for the manufacture of a medicament for the treatment or prevention of asthma or adult respiratory distress syndrome.

It is also an object of the present invention to provide the use of a compound of formula I or a pharmaceutically acceptable salt or a prodrug thereof for the manufacture of a medicament for the treatment or prevention of septic shock.

It is also an object of the present invention to provide the use of a compound of formula I or a pharmaceutically acceptable salt or a prodrug thereof for the manufacture of a medicament for the treatment or prevention of osteoporosis.

It is also an object of the present invention to provide the use of a compound of formula I or a pharmaceutically acceptable salt or a prodrug thereof for the manufacture of a medicament for the treatment or prevention of viral infections.

It is also an object of the present invention to provide the use of a compound of formula I or a pharmaceutically acceptable salt or a prodrug thereof for the manufacture of a medicament for the treatment or prevention of transplant rejection.

The present invention also provides the use of a compound of formula I or a pharmaceutically acceptable salt or a prodrug thereof for inhibiting the activation of the transcription factor NF-κB.

The present invention also provides the use of a compound of formula I or a pharmaceutically acceptable salt or a prodrug thereof for inhibiting the expression of genes which are dependent on and/or regulated by, at least partially, the transcription factor NF-κB.

The present invention also provides the use of a compound of formula I or a pharmaceutically acceptable salt or a prodrug thereof for the treatment or prevention of disorders associated with the activation of the transcription factor NF-κB and/or the expression of genes which are dependent on this transcription factor.

The present invention also provides the use of a compound of formula I or a pharmaceutically acceptable salt or a prodrug thereof for inhibiting the expression of COX-2.

The present invention also provides the use of a compound of formula I or a pharmaceutically acceptable salt or a prodrug thereof for the treatment or prevention of diseases mediated by COX-2, preferably rheumatoid arthritis and other arthritic conditions, arthrosis, preterm labour, dementia or cancer.

The present invention also provides the use of a compound of formula I or a pharmaceutically acceptable salt or a prodrug thereof for inhibiting the expression of VCAM-1.

The present invention also provides the use of a compound of formula I or a pharmaceutically acceptable salt or a prodrug thereof for the treatment or prevention of diseases mediated by VCAM-1, preferably atherosclerosis, rheumatoid arthritis, lupus, multiple sclerosis, inflammatory bowel disease, asthma, allergic rhinitis and tumor metastasis.

The present invention also provides the use of a compound of formula I or a pharmaceutically acceptable salt or a prodrug thereof for inhibiting the expression of iNOS.

The present invention also provides the use of a compound of formula I or a pharmaceutically acceptable salt or a prodrug thereof for the treatment or prevention of diseases mediated by iNOS, preferably inflammation, septic shock, inflammatory bowel disease and neurodegenerative diseases.

The present invention also provides the use of a compound of formula I or a pharmaceutically acceptable salt or a prodrug thereof for inhibiting the expression of TNF-α.

The present invention also provides the use of a compound of formula I or a pharmaceutically acceptable salt or a prodrug thereof for the treatment or prevention of diseases mediated by TNF-α, preferably rheumatoid arthritis, rheumatoid spondylitis, gouty arthritis and other arthritic conditions, arthrosis, sepsis, septic shock, endotoxic shock, toxic shock syndrome, adult respiratory distress syndrome, cerebral malaria, chronic pulmonary inflammatory disease, silicosis, pulmonary sarcoidosis, pulmonary fibrosis, hepatitis, osteoporosis and other bone resorption diseases, reperfusion injury, transplant rejection, multiple sclerosis, lupus, fever and myalgias due to infections, cachexia, acquired immune deficiency syndrome (AIDS), inflammatory bowel disease and pyresis.

The present invention also provides the use of a compound of formula I or a pharmaceutically acceptable salt or a prodrug thereof for inhibiting the expression of MCP-1.

The present invention also provides the use of a compound of formula I or a pharmaceutically acceptable salt or a prodrug thereof for the treatment or prevention of diseases mediated by MCP-1, preferably atherosclerosis, glomerulonephritis, rheumatoid arthritis, pulmonary fibrosis, restenosis, asthma, psoriasis, inflammatory bowel disease, multiple sclerosis and transplant rejection.

The present invention also provides a method for inhibiting the activation of the transcription factor NF-κB in a mammal in need thereof, which comprises administering to said mammal a therapeutically effective amount of a compound of formula I or a pharmaceutically acceptable salt or a prodrug thereof. The mammal is preferably a human being.

The present invention also provides a method for inhibiting the expression of genes which are dependent on and/or regulated by, at least partially, the transcription factor NF-κB in a mammal in need thereof, which comprises administering to said mammal a therapeutically effective amount of a compound of formula I or a pharmaceutically acceptable salt or a prodrug thereof.

The present invention also provides a method for the treatment or prevention of disorders associated with the activation of the transcription factor NF-κB and/or the expression of genes which are dependent on this transcription factor in a mammal in need thereof, which comprises administering to said mammal a therapeutically effective amount of a compound of formula I or a pharmaceutically acceptable salt or a prodrug thereof.

The present invention also provides a method for inhibiting the expression of COX-2 in a mammal in need thereof, which comprises administering to said mammal a therapeutically effective amount of a compound of formula I or a pharmaceutically acceptable salt or a prodrug thereof.

The present invention also provides a method for the treatment or prevention of diseases mediated by COX-2, preferably rheumatoid arthritis and other arthritic conditions, arthrosis, preterm labour, dementia or cancer, in a mammal in need thereof, which comprises administering to said mammal a therapeutically effective amount of a compound of formula I or a pharmaceutically acceptable salt or a prodrug thereof.

The present invention also provides a method for inhibiting the expression of VCAM-1 in a mammal in need thereof, which comprises administering to said mammal a therapeutically effective amount of a compound of formula I or a pharmaceutically acceptable salt or a prodrug thereof.

The present invention also provides a method for the treatment or prevention of diseases mediated by VCAM-1, preferably atherosclerosis, rheumatoid arthritis, lupus, multiple sclerosis, inflammatory bowel disease, asthma, allergic rhinitis and tumor metastasis, in a mammal in need thereof, which comprises administering to said mammal a therapeutically effective amount of a compound of formula I or a pharmaceutically acceptable salt or a prodrug thereof.

The present invention also provides a method for inhibiting the expression of iNOS in a mammal in need thereof, which comprises administering to said mammal a therapeutically effective amount of a compound of formula I or a pharmaceutically acceptable salt or a prodrug thereof.

The present invention also provides a method for the treatment or prevention of diseases mediated by iNOS, preferably inflammation, septic shock, inflammatory bowel disease and neurodegenerative diseases, in a mammal in need thereof, which comprises administering to said mammal a therapeutically effective amount of a compound of formula I or a pharmaceutically acceptable salt or a prodrug thereof.

The present invention also provides a method for inhibiting the expression of TNF-α in a mammal in need thereof, which comprises administering to said mammal a therapeutically effective amount of a compound of formula I or a pharmaceutically acceptable salt or a prodrug thereof.

The present invention also provides a method for the treatment or prevention of diseases mediated by TNF-α, preferably rheumatoid arthritis, rheumatoid spondylitis, gouty arthritis and other arthritic conditions, arthrosis, sepsis, septic shock, endotoxic shock, toxic shock syndrome, adult respiratory distress syndrome, cerebral malaria, chronic pulmonary inflammatory disease, silicosis, pulmonary sarcoidosis, pulmonary fibrosis, hepatitis, osteoporosis and other bone resorption diseases, reperfusion injury, transplant rejection, multiple sclerosis, lupus, fever and myalgias due to infections, cachexia, acquired immune deficiency syndrome (AIDS), inflammatory bowel disease and pyresis, in a mammal in need thereof, which comprises administering to said mammal a therapeutically effective amount of a compound of formula I or a pharmaceutically acceptable salt or a prodrug thereof.

The present invention also provides a method for inhibiting the expression of MCP-1 in a mammal in need thereof, which comprises administering to said mammal a therapeutically effective amount of a compound of formula I or a pharmaceutically acceptable salt or a prodrug thereof.

The present invention also provides a method for the treatment or prevention of diseases mediated by MCP-1, preferably atherosclerosis, glomerulonephritis, rheumatoid arthritis, pulmonary fibrosis, restenosis, asthma, psoriasis, inflammatory bowel disease, multiple sclerosis and transplant rejection, in a mammal in need thereof, which comprises administering to said mammal a therapeutically effective amount of a compound of formula I or a pharmaceutically acceptable salt or a prodrug thereof.

It is also encompassed within the scope of the present invention a pharmaceutical composition which comprises a therapeutically effective amount of a compound of formula I or a pharmaceutically acceptable salt or a prodrug thereof for the treatment or prevention of disorders associated with the activation of the transcription factor NF-κB and/or the expression of genes which are dependent on this transcription factor, and more preferably for the treatment or prevention of inflammation; asthma; adult respiratory distress syndrome (ARDS); immunoinflammatory and autoimmune diseases such as rheumatoid arthritis and other arthritic conditions, multiple sclerosis, psoriasis, inflammatory bowel disease, lupus and glomerulonephritis; arthrosis; septic shock; atherosclerosis; cancer; osteoporosis; preterm labour; transplant rejection; neurodegenerative diseases such as dementia, including Alzheimer's disease, Parkinson's disease and amyotrophic lateral sclerosis; and viral infections.

The pharmaceutically acceptable salts of a compound of formula I include any of the salts commonly used in pharmaceutical chemistry, such as for example the salts with inorganic cations such as sodium, potassium, calcium, magnesium, lithium, aluminium, zinc, etc as well as the salts formed with ammonia and other pharmaceutically acceptable amines.

Throughout the present description, the term prodrug of a compound of formula I means any precursor compound of a compound of formula I that is capable of being metabolized and release in vivo a compound of formula 1, that is triflusal or HTB.

By NF-κB it is to be understood any member of the family of proteins known by this name.

By gene which is dependent on and/or regulated by, at least partially, the transcription factor NF-κB it is to be understood any gene having in its promoter region one or more NF-κB binding sites. The list of genes regulated by NF-κB mentioned above under the heading "Description of the prior art" is cited only as an example and it is not to be understood as limiting the scope of the invention in any way.

By disorder associated with the activation of the transcription factor NF-κB and/or the expression of genes which are dependent on this transcription factor it is to be understood any disease or pathological state where the activation of NF-κB and/or the proteins whose expression (i.e. the expression of the gene that encodes them) is regulated by this transcription factor are involved, at least partially. The lists of these diseases mentioned above are cited only as examples and thus are not to be understood as limiting the scope of the present invention in any case.

The term neurodegenerative diseases includes, among others, dementias, such as Alzheimer's disease; diseases involving movement dysfunction, such as Parkinson's disease; progressive ataxias; and amyotrophies of neuronal origin, such as amyotrophic lateral sclerosis.

By the term dementia it is to be understood any pathology characterized by an impairment of the cognitive functions, such as for example Alzheimer's disease, post-traumatic dementia or dementia following infection as well as mixed situations.

The term inflammatory bowel disease includes both ulcerative colitis and Crohn's disease as well as any other type of variant of inflammatory bowel disease.

The term transplant rejection refers both to tissue transplant rejection, such as for example graft-versus-host disease, as well as organ transplant rejection.

Processes for preparing triflusal or HTB are disclosed in the above-mentioned US patent (U.S. Pat. No. 4,096,252).

As mentioned above, the compounds of formula I inhibit the activation of the transcription factor NF-κB and therefore can be used to inhibit said activation in mammals, preferably in human beings. The dose of a compound of formula I necessary to modulate the activation of the transcription factor NF-κB, or any other use herein described, will depend upon the disorder to be treated, the severity of the symptoms, the age and body weight of the patient as well as the chosen route of administration. Any person skilled in the art will be able to readily determine the appropriate doses depending on these factors without having to incur in undue experimentation. In human therapy, doses will generally be in the range between about 30 mg and about 3000 mg daily of a compound of formula I, which can be administered in one or several dosage units. Depending on the particular disease to be treated and the patient's situation, however, doses outside this range might be needed, which, as mentioned above, may be readily determined by those skilled in the art without requiring undue experimentation.

The compounds of formula I can be administered in the form of any pharmaceutical formulation, the nature of which will depend, as it is well known, upon the route of administration and the nature of the disease to be treated. These pharmaceutical compositions can be prepared by conventional methods, using compatible, pharmaceutically-acceptable excipients or vehicles. Examples of such compositions include capsules, tablets, syrups, powders and granulates for the preparation of extemporaneous solutions, injectable preparations, etc. A preferred route of administration for the compounds of formula I is by the oral route. For example, they can be administered as hard gelatine capsules containing for example 50, 100, 200, 300, 400 or 500 mg of a compound of formula I or a pharmaceutically acceptable salt or a prodrug thereof.

Figure 1:
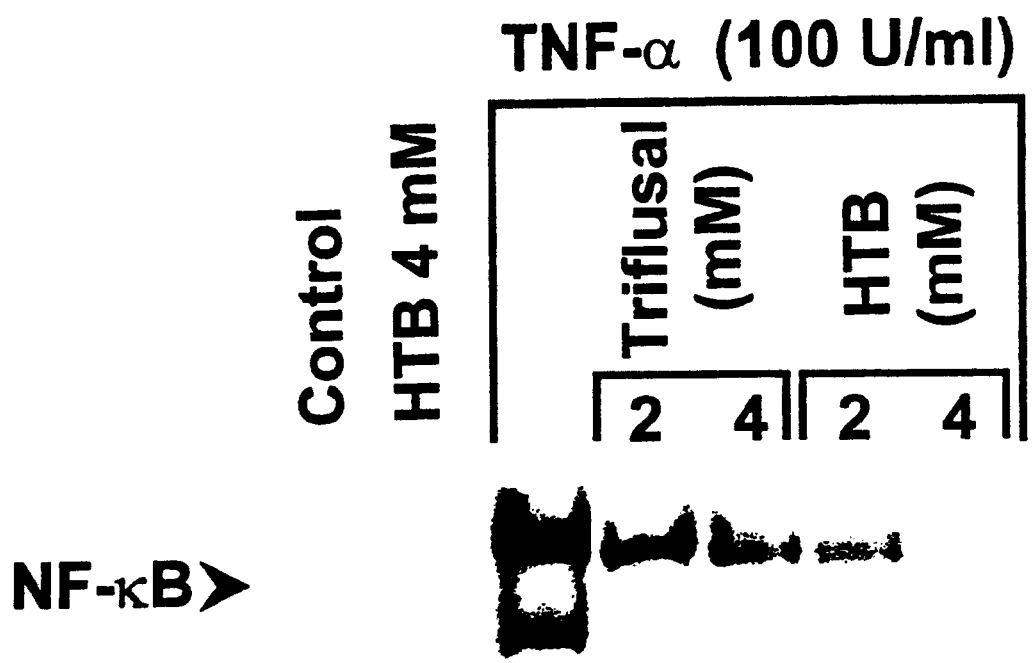
FIG. 1 shows the inhibitory effect of triflusal and HTB on the activation of the transcription factor NF-κB induced by TNF-α in human umbilical vein endothelial cell (HUVEC) cultures.

The following examples illustrate the utility of triflusal and HTB as inhibitors of the activation of NF-κB and its dependent genes. In any case are they to be construed as limiting the scope of the present invention. The following abreviations have been used in the examples:

EDTA: ethylenediaminetetraacetic acid
DTT: 1,4-dithiothreitol
bp: base pairs
PBS: phosphate-buffered saline
RT-PCR: reverse transcriptase polymerase chain reaction
dNTP: deoxyribonucleoside triphosphate
DNA: deoxyribonucleic acid
RNA: ribonucleic acid
MTT: thiazolyl blue
TBS: Tris-buffered saline
ATP: adenosyl triphosphate
DMSO: dimethylsulfoxide
FCS: fetal calf serum

EXAMPLE 1

Inhibition of the Activation of NF-κB Induced by TNF-α in HUVEC

A. Cell Culture

Human umbilical vein endothelial cells (HUVEC) were obtained by the procedure of Dejana et al. (*J. Cell Biol* 1987, 104(5), 1403–1411) by treatment of the umbilical vein with 0.2% collagenase P from *C. histolyticum* (Boehringer Mannheim GmbH, Manheim, Germany) for 20 minutes at 37° C. Next, cells were cultured in M199 medium (Flow Lab, Herts, U. K.) containing 100 U/ml penicillin, 100 μg/ml streptomycin, 2.5 μg/ml amphotericin B and 20% fetal calf serum. Primary cultures were plated in 25 cm² plastic flasks. After 24 hours cells were washed to remove those cells which had not adhered to the flask surface. Then, the same medium containing 10% fetal calf serum, 50 μg/ml endothelial cell growth supplement factor and 100 μg/ml heparin was added. After culturing for 5–7 days, cells reached confluence and were detached from the flask surface with 0.05% trypsin and 0.02% EDTA (Flow Lab). The reaction was inhibited by the addition of fetal calf serum, and then cells were washed and plated again in culture medium. Cells were grown to confluence in gelatin-coated flasks. Cells used for the experiments were from passages 2–7.

B. Treatment of HUVEC Cells with TNF-α and Electrophoretic Mobility Shift Assay (EMSA).

In this experiment, HUVEC cells were preincubated with Triflusal and HTB, at concentrations in both cases of 2 and 4 mM. Then these cells were stimulated with 100 U/ml TNF-α (Genzyme Diagnostics, Cambridge, Mass. USA) for 90 minutes. Next, HUVEC cells were washed with cold hypotonic lysis buffer (10 mM HEPES-KOH, pH 7.9, 10 mM KCl, 1.5 mM $MgCl_2$, 0.5 mM DTT (1,4-dithiothreitol), 0.5 mM phenylmethylsulfonyl fluoride, 5 μg/ml aprotinin, 5 μg/ml leupeptine and 0.6% Nonidet P-40) and were kept on ice for 10 minutes. Then, they were vortexed vigorously for 10 seconds. Unbroken cells were eliminated by centrifugation at 1,000×g for 10 minutes. The nuclei were collected by centrifugation at 15,000×g for 1 minute in a microcentrifuge. The nuclear pellet was resuspended in a high salt extraction buffer (25% glycerol and 0.5 M KCl). The nuclear extract was obtained by centrifugation for 30 minutes at 105,000×g in a Optima TI ultracentrifuge (Beckmann) using a TLA 100.2 rotor. A 22 bp double-stranded oligonucleotide containing NF-κB sequences was used as probe. This probe was end-labeled with (γ-$^{32}$P)ATP using T4 polynucleotide kinase and was purified by minicolumn chromatography. The κB sequence used was, 5'-AGTTCAGGGGAATTTCCCAGGC-3' and the complementary 5'-GCCTGGGAAATTCCCCTGAACT-3'. 10 μg of the purified nuclear protein was incubated for 20 minutes on ice with the radiolabeled oligonucleotide probe (2–6×10$^4$ cpm) in 25 μl of reaction buffer consisting of 2 μg poly(dI-dC), 10 mM Tris HCl pH 7.5, 100 mM NaCl, 1 mM EDTA, 1 mM DTT, 8% Ficoll and 4% glycerol. Nucleoprotein-oligonucleotide complexes were resolved by electrophoresis in a nondenaturing polyacrylamide gel in Tris-borate/EDTA buffer for 3 hours at 175 V and at 4° C. The gel was dried and autoradiographed with an intensifying screen at –80° C. and for 2 to 12 hours. The specificity of the DNA(probe)-protein complex was confirmed by competition of the $^{32}$P-labeled probe with a 300-fold excess of unlabeled probe, which showed no presence of the labeled probe in the DNA-protein complex (data not shown). The lane labeled as control corresponds to cells incubated for 90 minutes in the absence of TNF-α.

C. Results

The results of this experiment are shown in FIG. 1. Both triflusal and HTB concentration-dependently inhibit the activation of NF-κB induced by TNF-α in HUVEC.

EXAMPLE 2

Inhibition of the Activation of NF-κB Induced By Immune Complexes (IC) in Rat Macrophages A. Isolation and Culture of Rat Peritoneal Macrophages Rat peritoneal cavity cells were extracted and resuspended in DMEM culture medium in the absence of serum previously supplemented with 100 U/ml penicillin, 100 μg/ml streptomycin, 50 μg/ml gentamycin, 2 mM glutamine and 0.5 mM L-arginine. Cells were incubated for 2 hours in culture plates at 37° C. and those which had not adhered to the plates were removed by washing three times with the same fresh medium. More than 95% of the adherent cells were macrophages, as assessed by their ability to engulf zymosan particles and nonspecific esterase staining. Macrophages were kept at 37° C. under a 5% CO$_2$ atmosphere and two hours later non-adherent cells were removed and the peritoneal macrophages adhered to the plates were incubated with 100 μg/ml IgG/ovalbumin immune complexes prepared from rabbit antiserum for 2 hours in the presence or absence (vehicle) of triflusal or HTB (4 mM, both).

B. Electrophoretic Mobility Shift Assay (EMSA)

After incubation, macrophages were washed twice with PBS and the degree of activation (binding to DNA) of the transcription factor NF-κB was determined using the EMSA assay, described in detail in Example 1.

C. Results

Figure 2:
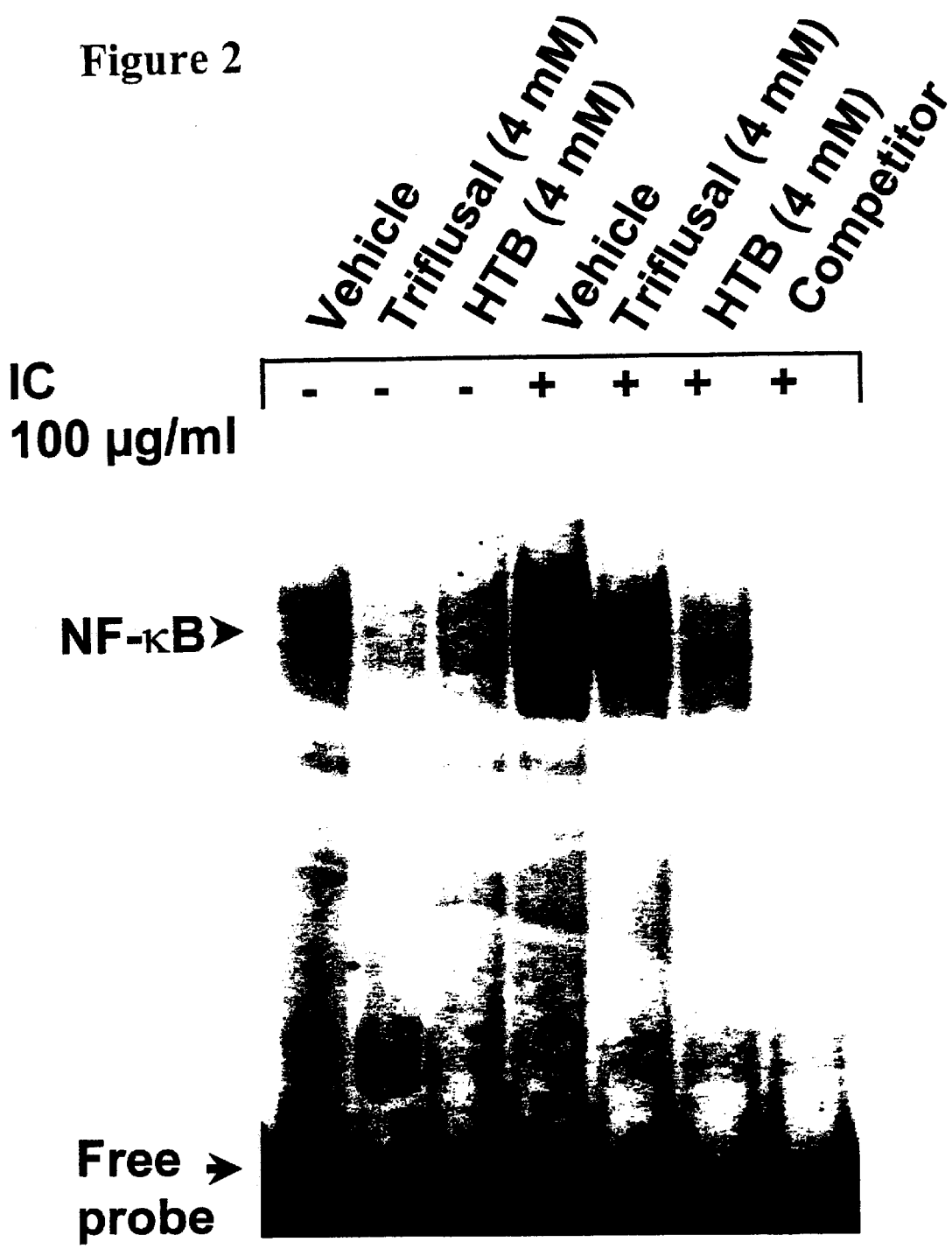
FIG. 2 shows the inhibitory effect of triflusal and HTB on the activation of the transcription factor NF-κB induced by immune complexes (IC) in rat macrophages.

FIG. 2 shows the results obtained with triflusal and HTB in this experiment. A representative example of the obtained in two independent experiments is shown. Both triflusal and HTB markedly inhibit the activation of NF-κB induced by immune complexes in rat macrophages.

EXAMPLE 3

Inhibition of the Activation of NF-κB Induced By Bacterial Lipopolysaccharide (LPS) in Human Peripheral Blood Mononuclear Cells (PBMC)

A. Isolation and Culture of Human Mononuclear Cells

Mononuclear cells (PBMC) were obtained from blood of healthy donors from the Hospital de Sant Pau (Barcelona) who had not taken any antiinflammatory drug during a period of not less than 2 weeks before blood extraction. Starting from a volume of about 80 ml of heparinized human blood (10 U/ml), this was diluted (1:1) with PBS (pH 7.4; Dulbecco) without calcium, magnesium nor sodium bicarbonate.

15 ml of Ficoll solution (d=1.077 at 20° C.; Biochrom KG) were placed in 50-ml Falcon tubes. To this solution a volume of about 25 ml per tube of the blood previously diluted with PBS was carefully added and the tubes were then centrifuged at 1,200 g for 20 minutes. Mononuclear cells concentrate on a whitish interphase between the plasma and the Ficoll solution. This interphase was collected with a Pasteur pipette and was diluted 1:1 with PBS. It was then centrifuged at 300 g for 10 min. The resulting pellet was resuspended in 50 ml PBS and was again centrifuged at 200 g for 10 min, in order to remove platelet contamination. Finally, the resulting pellet was resuspended in 20 ml of RPMI-1640 culture medium (GibcoBRL) supplemented with 10% fetal calf serum.

Isolated PBMCs were analyzed by standard Wright-Giemsa staining to examine if the cells displayed the morphological features of viable mononuclear cells and determine the different types of cells isolated (an average of 90% lymphocytes and 10% monocytes). Prior to the various treatments, cell viability was determined by the Trypan Blue exclusion assay. Cells were diluted at a concentration of 2.5 million/ml with RPMI medium containing 10% fetal calf serum and were incubated (37° C., 5% CO$_2$) 1 hour in 6-well plates (2 ml/well, 5 million PBMC) without adding any drug (control) or adding HTB (1–3 mM). Next, cells were incubated for further 10 minutes in the presence of 10 μg/ml E.coli lipopolysaccharide (LPS, 026:B6 serotype; Sigma). After incubation, a sample (100 μl) was taken in order to carry out a cell count as well as cell viability controls by measuring the ability of mitochondrial dehydrogenases to convert the soluble tetrazolium salt, MTT, into the insoluble product formazan (MTT assay). Cells were also incubated with HTB (3 mM) in the absence of LPS. In all cases, cell viability was equal to or higher than 95%.

B. Electerophoretic Mobility Shift Assay (EMSA)

After incubation, PBMCs were washed twice with PBS and the degree of activation (binding to DNA) of the transcription factor NF-κB was determined using the EMSA assay, described in detail in Example 1.

C. Results

Figure 3A:
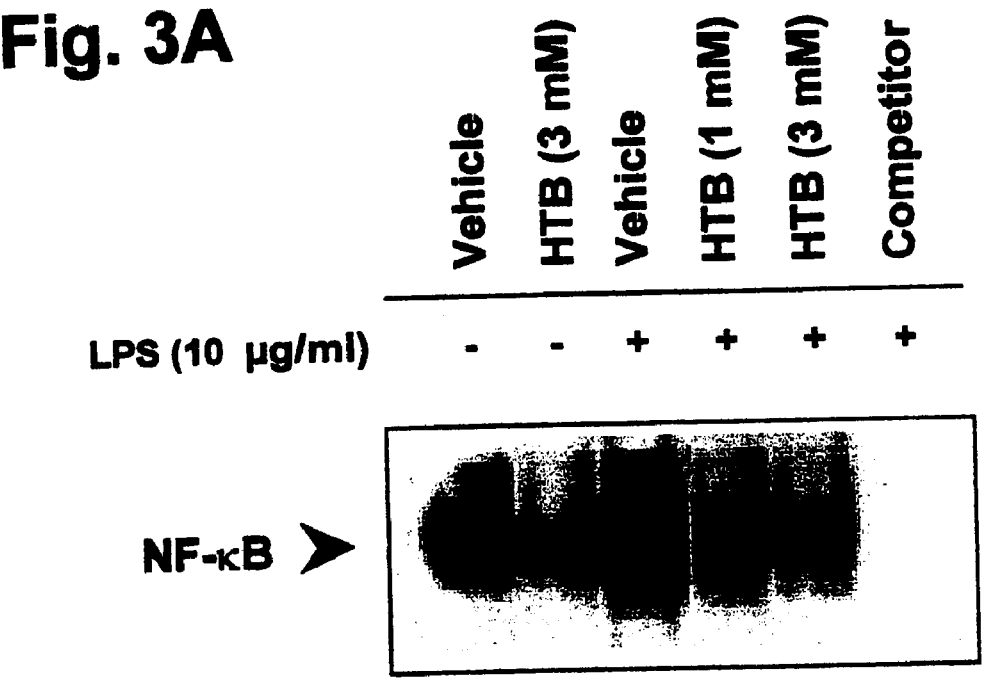
FIGS. 3(A and B) shows the inhibitory effect of HTB on the activation of the transcription factor NF-κB induced by bacterial lipopolysaccharide (LPS) in human peripheral blood mononuclear cells.
Figure 3B:
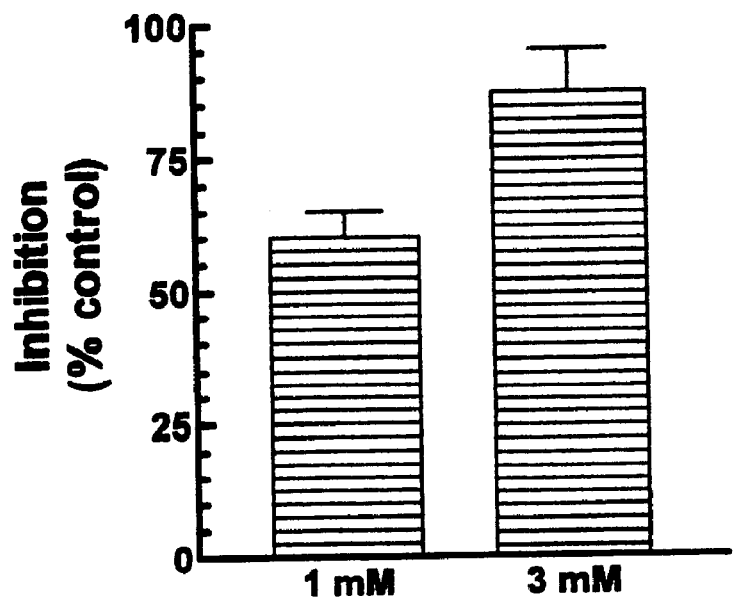

FIG. 3 shows the results obtained with HTB in this experiment. A representative example of the obtained in two independent experiments is shown. HTB markedly inhibits the activation of NF-κB induced by LPS in human PBMCs.

EXAMPLE 4

Inhibition of the Expression of VCAM-1 in HUVEC Induced By TNF-α

A. Synthesis of First Strand cDNA and PCR of VCAM-1

Primers used for the detection of VCAM-1 mRNA by RT-PCR were designed from the human gene sequence (EMBL/GenBank AC: M30257), using the Wisconsin Package Version 9.1, Genetics Computer Group (GCG), Madison, Wis. Their sequences were 5'-TGTCACTGTAAGCTGCAAG-3' and 5'-TTCCAGCCTGGTTAATTC-3', corresponding to nucleotides 1090–1108 and 1589–1572 (L. Osborn et al., *Cell* 1989, 59(6), 1203–1211). Total RNA was extracted from cultured cells using the guanidium isothiocyanate method (P. Chomczynski and N. Sacchi, *Anal Biochem.* 1987, 162(1), 156–159). cDNA first strand was synthesized from total RNA by reverse transcription reaction. The reaction was carried out using 0.2 mg/ml total RNA (preheated at 68° C. for 10 minutes), 2.5 µl H$_2$O, 20 U of RNAase inhibitor, 4 µl buffer 5×, 2 µl 0.1 M DTT, 4 µl 2.5 mM dNTP, 1 µl 0.1 mM hexanucleotides and 200 U of Moloney-murine leukemia virus reverse transcriptase. The reaction was carried out at 37° C., for 60 minutes in a volume of 20 µl. VCAM-1 cDNA was amplified by PCR in a reaction mixture containing 2 µl DNA, 10 µl H$_2$O, 2.5 µbuffer 10×, 0.75 µl 50 mM MgCl$_2$, 1.0 µl 2.5 mM dNTP, 1.25µl of each primer (sense and antisense) and 0.25 µl Taq DNA polymerase 5 U/ml. A negative control using water was included in each PCR reaction. The amplification conditions were as follows: an initial cycle of denaturation at 94° C. for 5 minutes, and then 30 cycles comprising: denaturation at 94° C. for 30 seconds, primer annealing at 59° C. for 30 seconds, and extension at 72° C. for 1 minute; and finally a cycle of extension at 72° C. for 7 minutes. The relative amounts of each amplified cDNA were determined by measuring the density of the bands stained with ethidium bromide using the Gel Doc documentation system and the Molecular Analyst software from Bio-Rad Laboratories, Hercules, Calif. The expression of β-actin was used as control for assaying the expression of a constitutively expressed gene.

Specifically, the effect of Triflusal (4 mM) and HTB (4 mM) on the regulation of the expression of VCAM-1 mRNA induced by TNF-α (100 U/ml) in HUVEC was studied. Thus, cells were incubated in the presence or absence of TNF-α and with Triflusal and HTB. After one hour, total RNA was extracted and subjected to the reverse transcription reaction. Then, an amplification reaction by PCR was carried out with the primers designed for the sequences of the molecules VCAM-1 and human β-actin. The PCR products were separated by electrophoresis in a 1.8% agarose gel and were later quantified. The molecular weight of the amplification products was determined from the electrophoretic migration of DNA size standards.

B. Results

Figure 4:
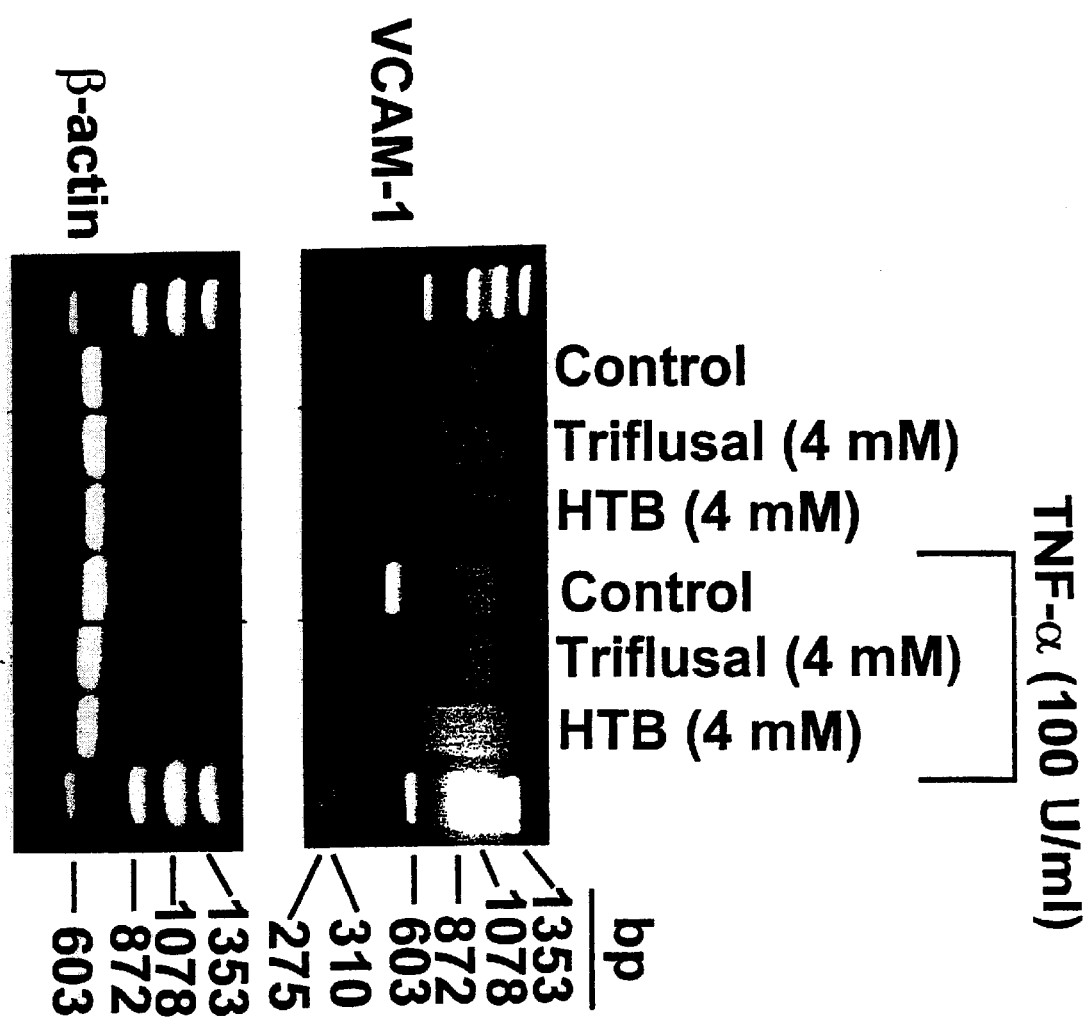
FIG. 4 shows the inhibitory effect of triflusal and HTB on the expression of VCAM-1 mRNA induced by TNF-α in HUVEC.

The results obtained in this experiment are shown in FIG. 4. Both triflusal and HTB at a concentration of 4 mM completely inhibit the expression of VCAM-1 mRNA induced by TNF-α in HUVEC. The absence of effect on the expression of β-actin mRNA shows the selectivity of the tested compounds for the transcription factor NF-κB.

EXAMPLE 5

Inhibition of the Expression of iNOS in Rat Peritoneal Macrophages Induced By Immune Complexes A. Determination of the Production of NO By Rat Peritoneal Macrophage Rat peritoneal cells were obtained and resuspended in DMEM culture medium in the absence of serum and supplemented with antibiotics. Macrophages were isolated by their ability to adhere to culture plates following incubation for 2 hours at 37° C. Non-adherent cells were removed and it was then checked that more than 95% of the adherent cells were macrophages, as assessed by their ability to engulf zymosan particles and nonspecific esterase staining. Culture plates were kept at 37° C. under a 5% CO$_2$ atmosphere, and the peritoneal macrophages adhered to the plates were incubated with 100 µg/ml IgG/ovalbumin immune complexes in the presence or absence (Control) of triflusal or HTB (0.1–20 mM, both). Drugs were added 10 minutes before the addition of IgG/ovalbumin and the production of NO was determined as the nitrite present after 24 hours.

B. Determination of NO and Nitrite iNOS expression was indirectly measured as the production of NO. NO released from macrophage cultures was determined indirectly by the accumulation of nitrites. To one milliliter of cell culture (0.5 million cells in medium without phenol red) was added 100 µl of a solution of 1 mM sulphanilic acid and 100 mM HCl (final concentration). After incubation for five minutes, the medium was aspirated and centrifuged in an eppendorf microcentrifuge. 50 µl naphthylenediamine (1 mM final concentration) were added and after 15 minutes of incubation the absorbance of the sample was measured at 548 nm and was compared with a NaNO$_2$ standard. The production of NO was expressed as nmol NO$_2^-$/mg protein.

C. Results

Figure 5A:
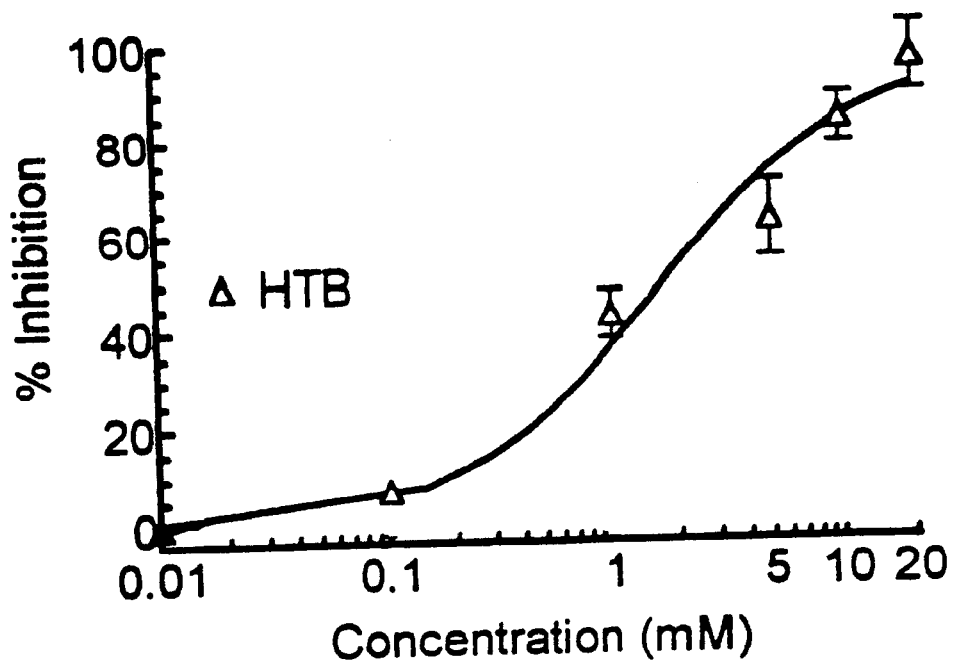
FIG. 5 shows the inhibitory effect of HTB (5A) and triflusal (5B) on the production of nitrite induced by immune complexes in rat macrophages.
Figure 5B:
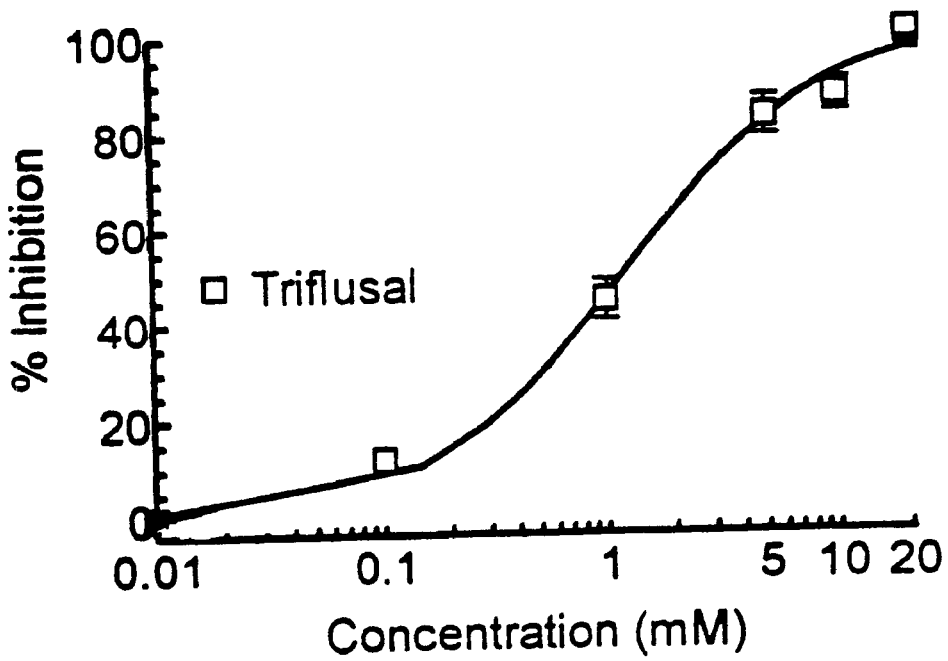
Figure 6A:
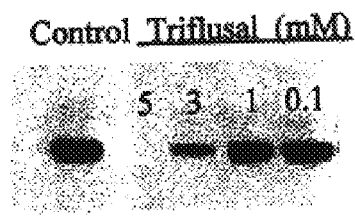
FIG. 6 shows the effect of triflusal and HTB on LPS-induced COX-2 in human mononuclear cells: (6A) inhibitory effect of triflusal on COX-2 expression; (6B) inhibitory effect of HTB on COX-2 expression; (6C) inhibition of prostaglandin $E_2$ ($PGE_2$) production elicited by triflusal; (6D) inhibition of $PGE_2$ production elicited by HTB.
Figure 6B:
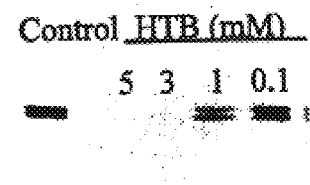
Figure 6C:
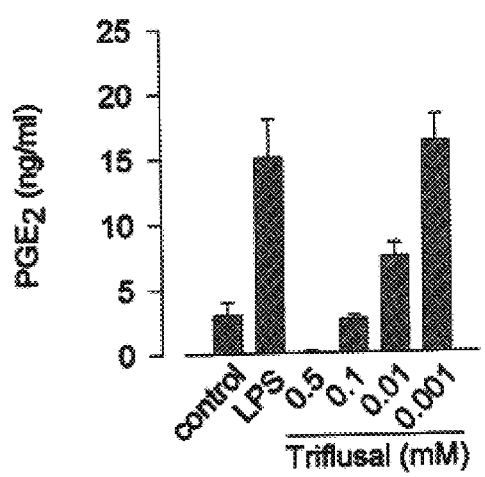
Figure 6D:
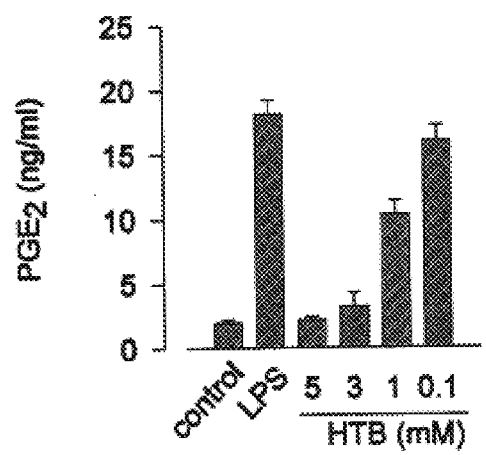

The results obtained in this experiment are shown in FIG. 5A for HTB and in FIG. 5B for triflusal. Points represent the mean ± standard error of the mean (SEM) from 7 to 9 experiments, each performed in duplicate. IC$_{50}$ values calculated for triflusal and HTB from the corresponding graphs were 1.13±0.12 and 1.84±0.34 mM, respectively. Similar results were obtained when macrophages were incubated with LPS instead of immune complexes.

EXAMPLE 6

Inhibition of COX-2 Expression Induced By Bacterial Lipopolysaccharide (LPS) in Human Peripheral Blood Mononuclear Cells (PBMC)

A. Isolation and Culture of Human Mononuclear Cells

Mononuclear cells (PBMC) were obtained from blood of healthy donors from the Hospital de Sant Pau (Barcelona) who had not taken any antiinflammatory drug during a period of not less than 2 weeks before blood extraction. Starting from a volume of about 80 ml of heparinized human blood (10 U/ml), this was diluted (1:1) with PBS (pH 7.4; Dulbecco) without calcium, magnesium nor sodium bicarbonate.

15 ml of Ficoll solution (d=1.077 at 20° C.; Biochrom KG) were placed in 50-ml Falcon tubes. To this solution a volume of about 25 ml per tube of the blood previously diluted with PBS was carefully added and the tubes were then centrifuged at 1,200 g for 20 minutes. Mononuclear cells concentrate on a whitish interphase between the plasma and the Ficoll solution. This interphase was collected with a Pasteur pipette and was diluted 1:1 with PBS. It was then centrifuged at 300 g, 10 min. The resulting pellet was resuspended in 50 ml PBS and was again centrifuged at 200 g for 10 min in order to remove platelet contamination. Finally, the resulting pellet was resuspended in 20 ml RPMI-1640 culture medium (GibcoBRL) supplemented with 10% fetal calf serum.

Isolated PBMCs were analyzed by standard Wright-Giemsa staining to examine if the cells displayed the morphological features of viable mononuclear cells and determine the different types of cells isolated (an average of 90% lymphocytes and 10% monocytes). Cells were diluted at a concentration of 2.5 million/ml with RPMI medium containing 10% fetal calf serum and were incubated (37° C., 5% CO$_2$) 19 hours in 6-well plates (2 ml/well, 5 million PBMC). Incubations were carried out in the presence of 10 µg/ml E.coli lipopolysaccharide (LPS, 026:B6 serotype; Sigma) without adding any drug (control) or adding Triflusal or HTB (0.1–5 mM). Prior to incubations, cell viability controls were performed using the Trypan Blue exclusion assay. After incubation, a sample (100 µl) was taken in order to perform a cell count as well as cell viability controls by measuring the ability of mitochondrial dehydrogenases to convert the soluble tetrazolium salt, MTT, into the insoluble product formazan (MTT assay). Cells were also incubated with HTB and Triflusal at the same concentrations but without adding LPS. In all cases, cell viability was equal to or higher than 95% both at the beginning of the experiment and after 19 hours incubation.

B. Immunoblot Assay

After incubation, cells were centrifuged for 5 min at 1,000 g. The supernatant was collected and stored at −70° C. for later determination of $PGE_2$ levels as a measure of COX-2 activity, and the pelleted cells were resuspended in 5 ml PBS and centrifuged again (5 min, 1,000 g). The resulting pellet was resuspended in 50 μl cell lysis buffer (PBS with 1% Nonidet-40 and 1 mM EDTA) and incubated in ice for 15 minutes. The resulting mixture was centrifuged at 20,000 g for 15 min and the supernatant was collected. 5 μl of the supernatant were taken and diluted 1/20 with PBS in order to determine the concentration of protein using the BCA Protein Assay Reagent (Pierce).

The remaining supernatant was then mixed in a 1:1 ratio with electrophoresis gel loading buffer (50 mM Tris; SDS, 2% w/v; glycerol, 10% v/v; β-mercaptoethanol, 50 μl/ml and bromophenol blue, 2 mg/ml) and boiled for 5 min. Samples were centrifuged at 10,000 g for 2 min and then subjected to discontinuous electrophoresis in SDS-Polyacrylamide gel (4% stacking gel/7.5% separating gel) at a variable intensity and a fixed voltage of 200V, until the front was only a few millimetres from the gel end (about 1 hour).

Proteins were transferred to a nitrocellulose membrane, using a cooled TE 22 Mighty Small Transfer Unit (Hoefer) system, at a voltage of 100 V for 2 hours. When the transfer was finished, membranes were stirred overnight at 4° C. in blocking buffer (1:4 dried fat-free milk in TBS containing 0.1% Tween 20).

Blocked membranes were incubated 1 hour under stirring with a goat polyclonal antibody raised against human COX-2 (Santa Cruz Biotechnology, Inc.), and after washing were incubated 1 hour with a horseradish peroxidase-labeled antibody (Rabbit Anti-goat IgG-Horseradish Peroxidase, Immunopure, Pierce) and the antibody bound to the protein was visualized by chemoluminescence (ECL, Amershan).

Finally, the supernatants from each experiment that had been stored at −70° C. were defrozen and the amount of $PGE_2$ in solution was determined using specific ELISA kits (Amershan-Biotrak RPN22).

C. Results

The results obtained in this experiment are shown in FIG. 6. The results shown correspond to two representative immunoblots from the obtained in five independent experiments (FIG. 6A: triflusal; FIG. 6B: HTB) and the mean ± SEM of the quantification of $PGE_2$ in the supernatants of the cultures corresponding to said experiments (FIG. 6C: triflusal; FIG. 6D: HTB). Both triflusal and HTB concentration-dependently inhibit COX-2 expression as well as $PGE_2$ production.

EXAMPLE 7
Inhibition of COX-2 Expression in Rat Inflammatory Exudate Cells

A. General Method

Lewis rats (175–200 g) were used in this study. Rats were randomly distributed in groups of 5 animals. An air pouch was produced by subcutaneous injection of 20 ml of sterile air into the intrascapular area of animals in each group. Every two days, 10 ml of air were injected again into the cavity to keep the space open. Seven days after the first injection of air, 2 ml of a 1% carrageenan solution was injected into the air pouch in all groups to produce an inflammatory reaction. Test compound was administered orally 30 min before carrageenan administration. The animals were killed 6 h later and the volume of exudate was measured. The type and number of cells present were determined using standard Wright-Giemsa staining and a Coulter Counter cell counter, respectively. The exudate was centrifuged at 400 g at 4° C. for 7 min and $PGE_2$ concentration was determined by enzyme-immunoassay (Amershan-Biotrak RPN222). The cell pellet was resuspended in 2 ml cold 0.85% NaCl. To eliminate red cell contamination, cells were subjected to a selective cellular lysis by the addition of 6 ml cold water for 20 seconds. The isotonicity of the cellular suspension was restored by the addition of 2 ml 3.5% NaCl. Finally, the cellular suspension was centrifuged under the same conditions mentioned above and the pellet was resuspended in lysis buffer at a density of $2 \times 10^8$ cells for immunoblot assays (see Example 6).

B. Results

Figures 7A, 7B:
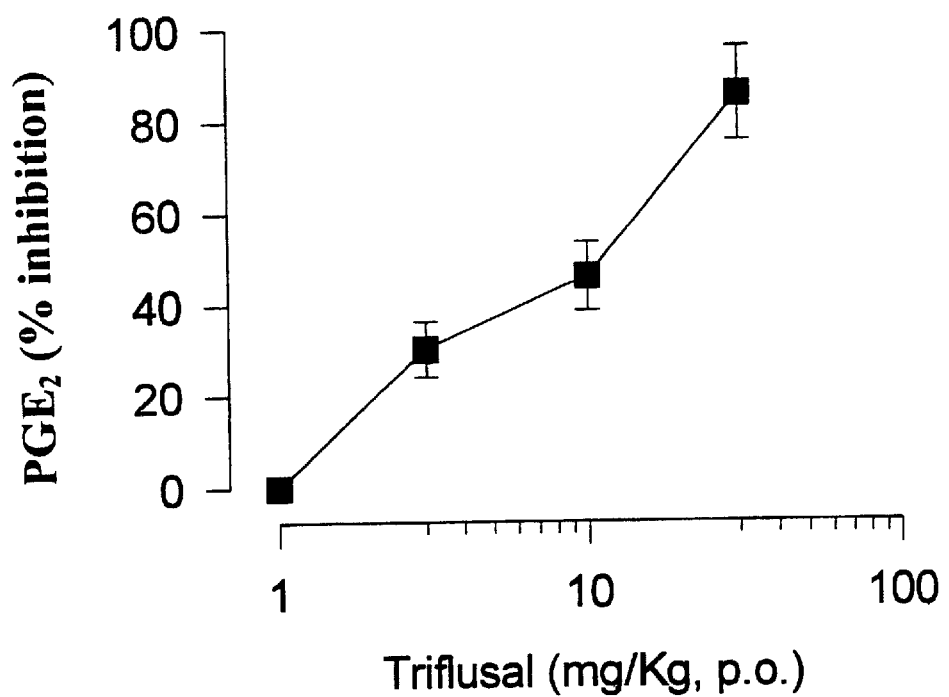
FIG. 7 shows the inhibitory effect of triflusal administered orally on COX-2 expression (7A) and on $PGE_2$ production (7B) in a carrageenan-induced inflammation model in the rat.

The results are shown in FIG. 7. FIG. 7A corresponds to a representative immunoblot and FIG. 7B shows the mean ± SEM of the quantification of $PGE_2$ in the rat exudate (n=4). The oral administration of triflusal (3–30 mg/kg) dose-dependently inhibits COX-2 expression in the cells present in the exudate as well as $PGE_2$ production.

EXAMPLE 8
Inhibition of the Expression of Monocyte Chemotactic Protein-1 (MCP-1) Induced By Immune Complexes in the Human Monocytic Cell line THP-1

A. Cell Culture and Determination of MCP-1 Levels

Human monocytic THP-1 cells ($3 \times 10^6$ cells/well) were cultured in plastic dishes in RPMI 1640 culture medium supplemented with penicillin (100 U/ml), streptomycin (100 μg/ml), gentamycin (50 μg/ml), glutamine (2 mM) and 2% heat-inactivated fetal calf serum. Cells were cultured in the presence of HTB (2 and 4 mM) or vehicle and were activated with 100 μg/ml immune complex aggregates (A-lgG). The production of soluble MCP-1 was determined by ELISA using a commercially available kit (R&D Systems Inc.; Minneapolis, Minn.). The detection limit of the system was 5 pg/ml.

B. Results

Figure 8:
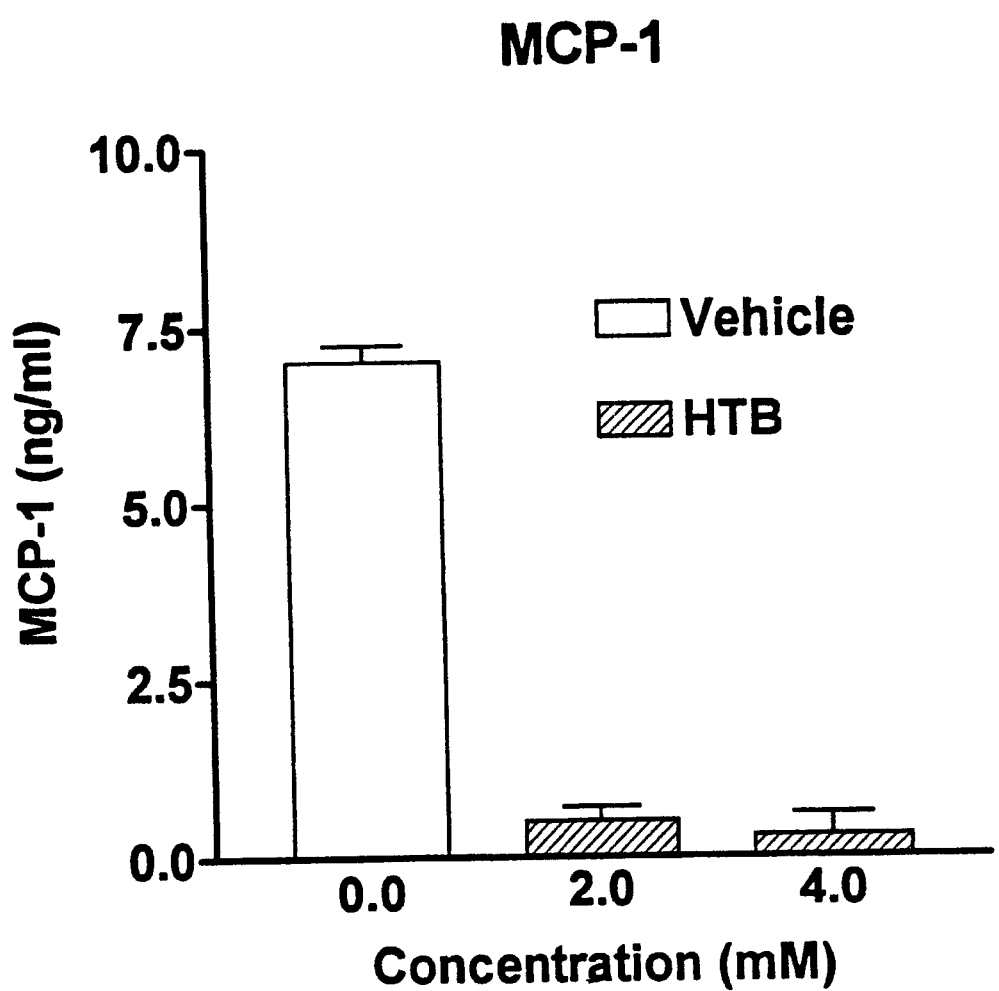
FIG. 8 shows the inhibitory effect of HTB on MCP-1 expression induced by immune complexes (IC) in human monocytic cell line THP-1.

The results obtained in this assay are shown in FIG. 8. HTB, both at a concentration of 4 mM and 2 mM, causes a complete inhibition of MCP-1 expression induced by immune complexes in THP-1.

EXAMPLE 9
Inhibition of the expression of TNF-α Induced By Bacterial Lipopolysaccharide (LPS) in Human Peripheral Blood Mononuclear Cells (PBMC)

A. Isolation and Culture of Human Mononuclear Cells

Mononuclear cells (PBMC) were obtained from blood of healthy donors from the Hospital de Sant Pau (Barcelona) following the procedure described in example 3. Cells were diluted at a concentration of 2 million/ml in RPMI medium supplemented with 10% fetal calf serum and were incubated (37° C., 5% $CO_2$) with triflusal, HTB or vehicle (DMSO) in the presence of 10 μg/ml $E.coli$ lipopolysaccharide (LPS, 026:B6 serotype; Sigma) for 19 hours. The cell suspension was then centrifuged at 2,000 g for 10 minutes at 4° C., and the resulting supernatant was stored at −70° C. for later analysis. The cytokine content was determined by enzymatic immunoassay, after 1/100 dilution of the samples.

B. Results

Figure 9:
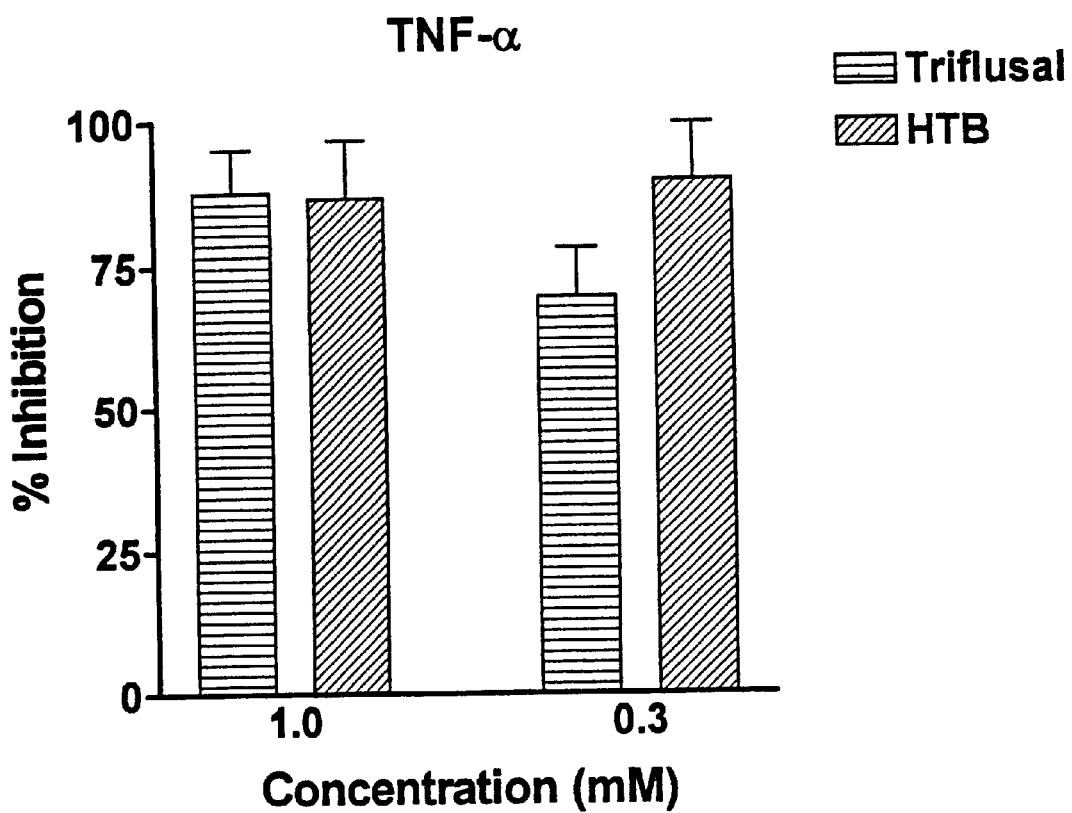
FIG. 9 shows the inhibitory effect of triflusal and HTB on TNF-α expression induced by bacterial lipopolysaccharide (LPS) in human peripheral blood mononuclear cells.

The results obtained with triflusal and HTB in this experiment are shown in FIG. 9. Both triflusal and HTB (1 and 0.3 mM) almost completely inhibit the LPS-induced TNF-α production. The results are expressed as the mean ± standard error of the mean from 2–5 separate experiments, each performed in triplicate.

EXAMPLE 10
Inhibition of the Activation of NF-κB in Post-natal Long Evans Black-hooded Rat Glial Cells A. General Method This study was carried out using post-natal (P9) Long Evans black-hooded rats. Each group consisted of 6 animals subjected to an experimental lesion, plus two control animals of the same age. The experimental lesion was induced by intracortical injection (sensorimotor area) of N-methyl-D-aspartate (NMDA), which causes a marked local neuronal degeneration. Triflusal (30 mg/kg) was administered orally in three doses (from day 7 to 9) every 24 hours. Glial reactivity was induced by NMDA injection at postnatal day 9, one hour after the last triflusal dose. At different times (2–24 h) after this last dose, animals were killed, brains were extracted and cut in a cryostat and sections were processed using immunocytochemical and histochemical techniques to determine NF-κB activation in microglia and astroglia using double staining: NF-κB-lectin and NF-κB-GFPA. In parallel, slices were cut on a vibratome to determine the degree of microglial and astroglial reactivity by histoenzymatic techniques (B. Castellano et al., *J.Histochem Cytochem.*, 1991, 39(5), 561–568).

B. Results

In control animals, cortical neurons but not glial cells showed constitutively activated NF-κB. This basal activation is inhibited by pretreatment with triflusal. In those animals where an excitotoxic lesion was performed with NMDA, a rapid activation of NF-κB was observed in glial cells. Pretreatment with triflusal at 30 mg/kg p.o. completely inhibited NF-κB activation, both in astroglial and microglial cells.

EXAMPLE 11

Triflusal Prevents Neuronal Cell Death in Cocultures of Neurons and Astrocytes Induced By Oxygen/Glucose Deprivation (OGD)

A. General Method

To carry out this study, an in vitro model of neuronal ischemia based on cocultures of neurons and glial cells was used. Primary cultures of type 1 astrocytes were prepared from 1-day old Wistar rats. Astrocytes were plated onto 60 mm, poly-D-lysine-coated plates. These cells were allowed to grow until they were confluent (about 11 days) and then rat primary neurons were plated onto them and were allowed to grow for 10 days. In addition, separate cultures of each one of the two types of cells were prepared.

Half of the cultures were exposed for four hours to oxygen-glucose deprivation (OGD), followed by a 24-hour recovery period. Both the cells exposed to OGD and control cells were treated at the start of OGD with 0, 10 and 30 µg/ml triflusal in a series of experiments and with 0, 20 and 100 µg/ml HTB in another series. After the 24-hour recovery period, the release of lactate dehydrogenase (LDH) into the medium was determined as a measure of cellular death, as well as the degree of apoptosis in the cultures (using the TUNEL assay) and total neuron and astrocyte counts present in the coculture (using Hoescht staining).

B. Results

In the cultures exposed to OGD a marked increase in LDH release as well as in the number of apoptotic neurons was observed, as compared to controls. The various concentrations of triflusal or HTB tested in this study completely inhibited both effects. Therefore, in this model both triflusal and its metabolite HTB can prevent apoptosis and neuronal degeneration induced by oxygen and glucose deprivation.

EXAMPLE 12

Inhibition of Adjuvant-induced Arthritis in the Rat

A. Arthritis Induction

Adjuvant-induced arthritis is characterized by the development, from day 14 after adjuvant injection, of a chronic inflammation of immunological origin in several joints, with accumulation of inflammatory cells and release of cytokines.

For this study, male Lewis rats with body weight between 100 and 150 g were used. Before the start of the study animals were acclimated for a period of at least 5 days. Animals were fasted for 18 hours before the study, with water ad libitum.

Throughout the study, animals were allowed free access to drinking water, except during observation periods.

Groups of five animals were randomized (Sham, Control and Triflusal). The duration of the study was 28 days. Arthritis was induced on day 1 of the study by subplantar administration of 0.1 ml of an emulsion formed with 10 mg *M. butyricum* and 10 ml Freund's incomplete adjuvant (Difco) to the right hindpaw of the animals from the Control and Triflusal groups. Sham animals received 0.1 ml Freund's incomplete adjuvant. Triflusal was administered daily from day 1 of the study at a dose of 10 mg/kg p.o. in Tween 80 (1%). On day 28 of the development of arthritis, the volume of the contralateral paw to that receiving the adjuvant injection was determined using a UGO BASILE 7150 plethysmometer. The inhibition of the increase in volume was calculated as follows:

$$Inh. = 100 - ((T-S)/(C-S))*100$$

Where: T=Triflusal group; C=Control group; and S=Sham group

B. Results

Oral administration of triflusal for 28 days at the dose of 10 mg/kg produced a 63.1±8.0% inhibition of the increase in volume of immunological origin induced by *M. butyricum* and adjuvant in control animals.

EXAMPLE 13

Study of the Viability of Various Cell Lines After Administration of HTB

A. General Method

Several cell lines obtained from the American Type Culture Collection (ATCC) were cultured at 37° C. and under a 5% $CO_2$ atmosphere. Each cell line was grown in an appropriate culture medium and within the exponential phase (Table I).

TABLE I

| CELL LINE | CULTURE MEDIUM |
| --- | --- |
| U-937 (human histiocytic lymphoma) | RPMI 1640 + 10% FCS |
| 143.98.2 (human osteosarcoma) | DMEM + 10% FCS |
| 1321N1 (human astrocytoma) | DMEM + 5% FCS + 0.5% Penicillin-Streptomycin |
| Jurkat (human acute T cell leukemia) | RPMI 1640 + 10% FCS |
| COLO 205 (human colon adenocarcinoma) | RPMI 1640 + 10% FCS |

For the cell viability studies 24-well plates were used, where $0.5 \times 10^6$ cells/ml (for 24-hour studies), $0.25 \times 10^6$ cells/ml (for 48-hour studies) or $0.125 \times 10^6$ cells/ml (for 72-hour studies) were incubated. Next, different concentrations of HTB (1–3 mM) were added and cells were incubated for different time periods (37° C., 5% $CO_2$). After incubation, the supernatant from each well was extracted, and cells were washed with culture medium without fetal calf serum. Then, the supernatant was extracted and 200 µl culture medium without fetal calf serum were added to each well. In addition, 20 μl substrate were added to determine cell viability. This method is based on the ability of viable cells to transform the colourless substrate into a coloured substance that is excreted to the supernatant (EZ4U, Biomedica Gmbh.). After incubating cells for 1 hour at 37° C. and 5% $CO_2$, 200 μl supernatant were collected and the absorbance was measured at 450 nm. The absorbance was also determined at 620 nm as a measure of the existing non-specific value.

B. Results

The results of cell viability determinations are shown on Table II. Incubation with HTB leads to the cell death of the various tumoral cell lines tested. This cell death is concentration- and time-dependent.

TABLE II

| | Percentage of cell viability. | | | | | |
|---|---|---|---|---|---|---|
| | 0 hours | 2 hours | 5 hours | 24 hours | 48 hours | 72 hours |
| U-937 | | | | | | |
| 1 mM HTB | 100 | 100 | 98.8 | 74.4 | 39.6 | 4.8 |
| 3 mM HTB | 100 | 96.1 | 92.6 | 13.9 | 7.5 | N.D. |
| JURKAT | | | | | | |
| 1 mM HTB | 100 | 100 | 76.8 | 11.3 | 3.6 | 1.6 |
| 3 mM HTB | 100 | 100 | 62.6 | 6.2 | 5.4 | N.D. |
| 1321N1 | | | | | | |
| 1 mM HTB | 100 | 99.7 | 94.2 | 87.5 | 67.6 | N.D. |
| 3 mM HTB | 100 | 85.3 | 67.2 | 62.2 | 17.8 | N.D. |
| COLO 205 | | | | | | |
| 1 mM HTB | 100 | 100 | 87.2 | 84.8 | 37.4 | 7.6 |
| 3 mM HTB | 100 | 94.5 | 69.2 | 39.6 | 14.3 | N.D. |
| 143.98.2 | | | | | | |
| 1 mM HTB | 100 | 100 | 100 | 93.9 | 83.2 | 50.4 |
| 3 mM HTB | 100 | 98.1 | 82.7 | 52.2 | 16.1 | N.D. |

N.D.: not determined

The results from the assays described in examples 1, 2 and 3 show that triflusal and HTB inhibit the activation of the transcription factor NF-κB. They also show that this inhibition is independent of the inducing agent and the type of cell. These results show the utility of triflusal and HTB in the treatment or prevention of those disorders where NF-κB is involved.

The results from example 4 show that triflusal and HTB inhibit VCAM-1 expression. It has been described that the VCAM-1 gene has NF-κB binding sites (C. Weber et al., Arterioscler. Thromb. 1994, 14(10), 1665–1673). It has been shown that adhesion molecules such as VCAM-1 are involved in disorders such as atherosclerosis (K. D. O'Brien et al., J. Clin. Invest. 1993, 92, 945–951), rheumatoid arthritis, lupus, multiple sclerosis, inflammatory bowel disease, asthma, allergic rhinitis and tumor metastasis. By inhibiting NF-κB activation and VCAM-1 expression, both triflusal and HTB may be of particular utility in the treatment or prevention of VCAM-1-mediated disorders such as all those mentioned above and specially atherosclerosis.

In example 5 it is shown that triflusal and HTB also inhibit iNOS expression, which is regulated at transcriptional level, at least partially, by NF-κB (U. Förstermann et al., Biochem. Pharmacol. 1995, 50(9), 1321–1332). It has been shown that iNOS is involved in pathologies such as inflammation, septic shock, inflammatory bowel disease and neurodegenerative diseases such as dementia and Parkinson's disease (J. E. Ogden and P. K. Moore, Trends Biotechnol. 1995, 13(2), 70–78). By inhibiting NF-κB activation and iNOS expression, triflusal and HTB may be of particular utility in the treatment or prevention of iNOS-mediated disorders and specially inflammation, septic shock, inflammatory bowel disease and neurodegenerative diseases such as dementia and Parkinson's disease.

The results of examples 6 and 7 show that triflusal and HTB inhibit COX-2 expression both in vitro and in vivo. It has been described that the gene encoding COX-2 has NF-κB binding sites (S. B. Appleby et al., Biochem. J. 1994, 302, 723–727). COX-2 has been associated with pathologies such as rheumatoid arthritis and other arthritic conditions, arthrosis, preterm labour, dementia, particularly Alzheimer's disease (T. A. Sandson and O. Felician, Exp. Opin. Invest. Drugs 1998, 7(4), 519–526), and cancer (M. Oshima et al., Cell 1996, 87(5), 803–809; K. Subbaramaiah et al., Cancer Res. 1996, 56(19), 4424–4429). By inhibiting NF-κB activation and COX-2 expression, triflusal and HTB may be of particular utility in the treatment or prevention of COX-2-mediated disorders and specially rheumatoid arthritis and other arthritic conditions, arthrosis, preterm labour, dementia and cancer.

The results from example 8 show that HTB inhibits also MCP-1 expression, which is regulated at transcriptional level, at least partially, by NF-κB (T. Martin et al., Eur. J. Immunol. 1997, 27(5), 1091–1097). It has been described that an excessive or unregulated MCP-1 production is involved in disorders such as glomerulonephritis (B. H. Rovin et al., Lab. Invest 1994, 71(4), 536–542), rheumatoid arthritis (P. M. Villiger et al., J. Immunol. 1992, 149(2), 722–727), pulmonary fibrosis (H. N. Antoniades et al., Proc. Nati. Acad. Sci. USA 1992, 89(12), 5371–5375), restenosis, asthma, psoriasis, inflammatory bowel disease, multiple sclerosis and transplant rejection, and it is the most potent chemotactic factor detected in macrophage-rich atherosclerotic plaques (S. Yla-Herttuala et al., Proc. Natl. Acad. Sci. USA 1991, 88(12), 5252–5256). By inhibiting NF-κB activation and MCP-1 expression, triflusal and HTB may be of particular utility in mentioned above.

The results from example 9 show that triflusal and HTB inhibit also the expression of TNF-α, which is regulated at transcriptional level, at least partially, by NF-κB (J. Yao et al, J. Biol. Chem. 1997, 272(28), 17795–17801). It has been described that an excessive or unregulated TNF-α production is involved in a broad range of disorders such as rheumatoid arthritis, rheumatoid spondylitis, gouty arthritis and other arthritic conditions, arthrosis, sepsis, septic shock, endotoxic shock, toxic shock syndrome, adult respiratory distress syndrome, cerebral malaria, chronic pulmonary inflammatory disease, silicosis, pulmonary sarcoidosis, pulmonary fibrosis, hepatitis, osteoporosis and other bone resorption disorders, reperfusion injury, transplant rejection, multiple sclerosis, lupus, fever and myalgias due to infections, cachexia, acquired immune deficiency syndrome (AIDS), inflammatory bowel disease and pyresis (L. Sekut and K. M. Connolly, Drug News Perspect. 1996, 9(5), 261–269). By inhibiting NF-κB activation and TNF-α expression, triflusal and HTB may be of particular utility in the treatment or prevention of TNF-α-mediated disorders such as those mentioned above.

The results from examples 11, 12 and 13 further show the usefulness of triflusal and HTB for the treatment or prevention of neurodegenerative diseases, arthritis and cancer, respectively.

The concentrations at which effects are observed in the experiments described in examples 1 to 13 are reached at the therapeutic doses of triflusal commonly used in humans by the oral route.

Without wishing to be bound by what is herein stated, it is believed that the inhibition of the expression of proteins such as VCAM-1, iNOS, COX-2, MCP-1 and TNF-α by triflusal and HTB is mediated, at least partially, by an inhibition of the activation of the transcription factor NF-κB. This notwithstanding, it is known that the expression of the genes that encode these proteins may be activated by other agents. Since we have shown that triflusal and HTB inhibit the expression of these genes (both in vitro and in vivo, in the case of COX-2), both products may also be useful in the treatment or prevention of disorders where there is an elevated expression of these genes that is independent of NF-κB, which is also encompassed by the scope of the present invention.

What is claimed is:

1. A method for the treatment or prevention of a disease in a warm-blooded animal in need thereof, wherein said disease is mediated by COX-2, which comprises administering to said animal an effective amount of a compound of formula I

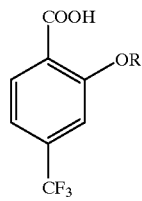
(I)

wherein R represents hydrogen or COCH$_3$, or a pharmaceutically acceptable salt or a prodrug thereof, wherein the disease mediated by COX-2 is selected from the group consisting of rheumatoid arthritis and other arthritic conditions, arthrosis, preterm labor and cancer.

2. A method for the treatment or prevention of a disease in a warm-blooded animal in need thereof, wherein said disease is mediated by iNOS, which comprises administering to said animal an effective amount of a compound of formula I

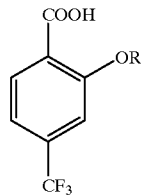
(I)

wherein R represents hydrogen or COCH$_3$, or a pharmaceutically acceptable salt or a prodrug thereof, wherein the disease mediated by iNOS is a member of the group consisting of inflammation, septic shock and inflammatory bowel disease.

3. A method for the treatment or prevention of a disease in a warm-blooded animal in need thereof, wherein said disease is mediated by TNF-α, which comprises administering to said animal an effective amount of a compound of formula I

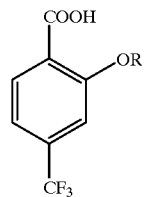
(I)

wherein R represents hydrogen or COCH$_3$, or a pharmaceutically acceptable salt or a prodrug thereof, wherein the disease mediated by TNF-α is selected from the group consisting of rheumatoid arthritis, rheumatoid spondylitis, gouty arthritis and other arthritic conditions, arthrosis, sepsis, septic shock, endotoxic shock, toxic shock syndrome, adult respiratory distress syndrome, cerebral malaria, chronic pulmonary inflammatory disease, silicosis, pulmonary sarcoidosis, pulmonary fibrosis, hepatitis, osteoporosis and other bone resorption diseases, reperfusion injury, transplant rejection, multiple sclerosis, lupus, fever and myalgia due to infections, cachexia, acquired immune deficiency syndrome (AIDS), inflammatory bowel disease and pyresis.

4. A method for the treatment or prevention of Parkinson's disease or amyotrophic lateral sclerosis in a warm-blooded animal in need thereof, comprising administering to said animal an effective amount of a compound of formula I

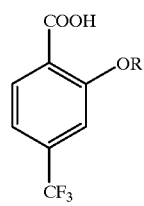
(I)

wherein R represents hydrogen or COCH$_3$, or a pharmaceutically acceptable salt or prodrug thereof.

5. A method for the treatment or prevention of an immunoinflammatory or autoimmune disease in a warm-blooded animal, comprising administering to said animal an effective amount of a compound of formula I

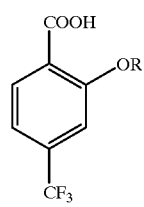
(I)

wherein R represents hydrogen or COCH$_3$, or a pharmaceutically acceptable salt or a prodrug thereof.

6. The method of claim 5 where the immunoinflammatory or autoimmune disease is a disease selected from the group consisting of rheumatoid arthritis and other arthritic conditions, multiple sclerosis, psoriasis, inflammatory bowel disease, lupus and glomerulonephritis.

7. A method for the treatment or prevention of arthrosis in a warm-blooded animal in need thereof, comprising administering to said animal an effective amount of a compound of formula I

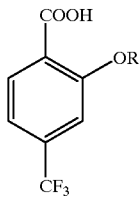

wherein R represents hydrogen or $COCH_3$, or a pharmaceutically acceptable salt or a prodrug thereof.

8. A method for the treatment or prevention of cancer in a warm-blooded animal in need thereof, comprising administering to said animal an effective amount of a compound of formula I

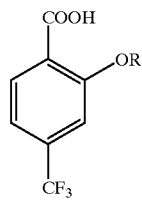

wherein R represents hydrogen or $COCH_3$, or a pharmaceutically acceptable salt or a prodrug thereof.

9. A method for the treatment or prevention of inflammation in a warm-blooded animal in need thereof, comprising administering to said animal an effective amount of a compound of formula I

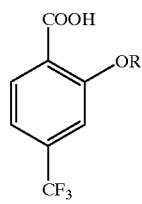

wherein R represents hydrogen or $COCH_3$, or a pharmaceutically acceptable salt or a prodrug thereof.

10. A method for the treatment or prevention of asthma or adult respiratory distress syndrome in a warm-blooded animal in need thereof, comprising administering to said animal an effective amount of a compound of formula I

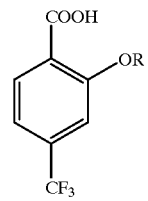

wherein R represents hydrogen or $COCH_3$, or a pharmaceutically acceptable salt or a prodrug thereof.

11. A method for the treatment or prevention of septic shock in a warm-blooded animal in need thereof, comprising administering to said animal an effective amount of a compound of formula I

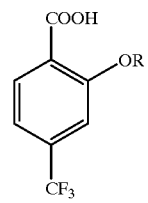

wherein R represents hydrogen or $COCH_3$, or a pharmaceutically acceptable salt or a prodrug thereof.

12. A method for the prevention of preterm labor in a warm-blooded animal in need thereof, comprising administering to said animal an effective amount of a compound of formula I

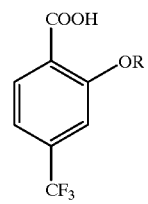

wherein R represents hydrogen or $COCH_3$, or a pharmaceutically acceptable salt or a prodrug thereof.

13. A method for the treatment or prevention of osteoporosis in a warm-blooded animal in need thereof, comprising administering to said animal an effective amount of a compound of formula I

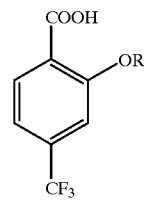

wherein R represents hydrogen or COCH$_3$, or a pharmaceutically acceptable salt or a prodrug thereof.

14. A method for the treatment or prevention of a viral infection in a warm-blooded animal in need thereof, comprising administering to said animal an effective amount of a compound of formula I

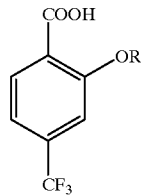

(I)

wherein R represents hydrogen or COCH$_3$, or a pharmaceutically acceptable salt or a prodrug thereof.

15. A method for the treatment or prevention of transplant rejection in a warm-blooded animal in need thereof, comprising administering to said animal an effective amount of a compound of formula I

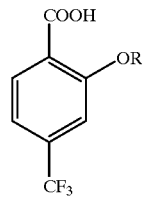

(I)

wherein R represents hydrogen or COCH$_3$, or a pharmaceutically acceptable salt or a prodrug thereof.

* * * * *